United States Patent [19]
Felix et al.

[11] Patent Number: 5,707,930
[45] Date of Patent: Jan. 13, 1998

[54] 4-CYCLOALKYL-5-SUBSTITUTED PYRIMIDINE COMPOUNDS USEFUL AS CROP PROTECTION AGENTS

[75] Inventors: Raymond A. Felix, Richmond; Hsiao-Ling M. Chin, Moraga; Frank X. Woolard, Greenbrae; David L. Lee, Pleasant Hill; David B. Kanne, Corte Madera, all of Calif.

[73] Assignee: Zeneca Limited, London, England

[21] Appl. No.: 715,293

[22] Filed: Sep. 16, 1996

[51] Int. Cl.⁶ .................. C07D 403/06; C07D 401/06; A01N 43/40; A01N 43/54
[52] U.S. Cl. .................. 504/197; 504/219; 504/221; 504/225; 504/239; 504/242; 504/243; 544/58.6; 544/60; 544/122; 544/243; 544/296
[58] Field of Search .................. 544/243, 296, 544/122, 60, 58.6; 504/239, 242, 243, 219, 221, 225, 197; 540/598

Primary Examiner—Matthew V. Grumbling
Attorney, Agent, or Firm—Joseph R. Snyder

[57] ABSTRACT

Herbicidal 4-cycloalkyl-5-substituted pyrimidine compounds of the formula

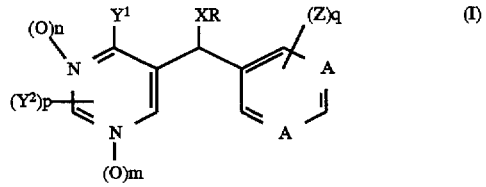

are described. Herbicidal compositions containing such substituted-pyrimidinyl compounds and methods of controlling undesirable vegetation employing these compounds are also disclosed. The compounds in which $XR$, is hydroxyl are also useful as intermediates for producing the disclosed substituted-pyrimidinyl derivatives.

19 Claims, No Drawings

4-CYCLOALKYL-5-SUBSTITUTED PYRIMIDINE COMPOUNDS USEFUL AS CROP PROTECTION AGENTS

FIELD OF THE INVENTION

In one aspect, this invention relates to novel 4-cycloalkyl-5-substituted pyrimidine compounds which exhibit desirable herbicidal activity. In other aspects, this invention relates to herbicidal compositions comprising a 4-cycloalkyl-5-substituted pyrimidine compound and a suitable carrier therefor, to a method of controlling undesirable vegetation comprising applying to the area where control is desired an herbicidally effective amount of a 4-cycloalkyl-5-substituted pyrimidine compound and to intermediates useful in making such compounds.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds. Further, it is an object of this invention to provide intermediates which, as well as exhibiting herbicidal activity, are also useful in the production of other herbicidally active compounds.

While certain hydroxybenzyl-substituted nitrogen-containing aryl compounds are disclosed in the art, these disclosures contain no description of the utility of such compounds. Thus, Radinov et al., "Synthesis of 4-Amino-3-pyridinyl and 4-Amino-5-pyrimidinyl Aryl Ketones and Related Compounds via an ortho-Lithiation Reaction", *Synthesis*, pp. 886–891 (November 1986), disclose inter alia at page 887, compounds of the formula

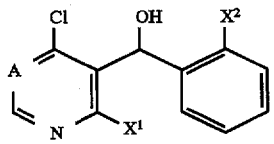

wherein A is CH or N, and when A is CH, $X^1$ is H and $X^2$ is hydrogen, chlorine or fluorine, and when A is N, $X^1$ is chlorine and $X^2$ is hydrogen.

Somewhat similarly, Marsais et al., "Directed Lithiation of 4-Halopyridines: Chemoselectivity, Regioselectivity and Application to Synthesis", *J. Heterocyclic Chem.*, Vol 25, pp. 81–87 (1987), disclose the production of compounds of the formula

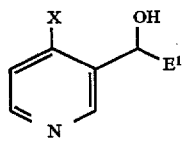

wherein $E^1$ is phenyl or 2-methoxyphenyl.

Certain (non-substituted)-pyridyl-3-carbinols of the formula

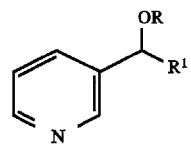

are disclosed in U.S. Pat. No. 4,407,806 to Cherpeck (wherein R and $R^1$ are as defined therein).

Similarly, U.S. Pat. No. 4,116,665 to Krumkalns discloses a method of regulating the growth of aquatic weeds employing compounds of the formula

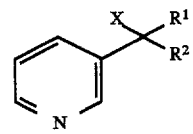

wherein, inter alia, $R^1$ may be hydrogen, $R^2$ may be (substituted)-phenyl and X may be hydroxyl or alkoxy.

Further, commonly owned U.S. Pat. No. 5,308,826, issued May 3, 1994, describes herbicidal 4-substituted pyridyl-3-carbinols and PCT publication Nos. WO 95/29898 and WO 95/29893 which describe hydroxyaryl-substituted heteroaryl compounds are incorporated herein by reference.

SUMMARY OF THE INVENTION

In one aspect, this invention is directed to a compound of the formula (I):

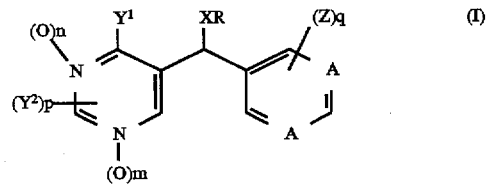

wherein

Z is independently halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —C(X)—$R^{10}$ or —S(O)$_k$—$R^{10}$;

q is 0, 1, 2, 3, 4 or 5;

A is C or N;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —S(O)$_k$—$R^{10}$ or —N($R^{11}$)($R^{12}$), wherein k, $R^{10}$, $R^{11}$ and $R^{12}$ have the same meanings as above; n and m are each independently 0 or 1; and p is 0, 1, or 2; or an agriculturally acceptable salt thereof.

In another aspect, this invention is directed to a herbicidal composition comprising:

(A) a compound of the formula (I):

$$(O)_m \quad Y^1 \quad XR \quad (Z)_q \quad (I)$$

(with structure drawing)

wherein:

Z is independently halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —C(X)—$R^{10}$ or —S(O)$_k$—$R^{10}$;

q is 0, 1, 2, 3, 4 or 5;

A is C or N;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —S(O)$_k$—$R^{10}$ or —N($R^{11}$)($R^{12}$), wherein k, $R^{10}$, $R^{11}$ and $R^{12}$ have the same meanings as above; n and m are each independently 0 or 1; and p is 0, 1, or 2; or an agriculturally acceptable salt thereof; and (B) a carrier therefor.

In yet another aspect, this invention is directed to a method for controlling undesirable vegetation comprising applying to the area where control is desired an herbicidally effective mount of a compound of the formula (I):

$$(O)_m \quad Y^1 \quad XR \quad (Z)_q \quad (I)$$

(with structure drawing)

wherein

Z is independently halogen, $C_1$–$C_6$ alkyl, $C_2$–$C_6$ alkenyl, $C_2$–$C_6$ alkynyl, nitro, cyano, hydroxy, thiocyano, —N($R_{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —C(X)—$R^{10}$ or —S(O)$_k$—$R^{10}$;

q is 0, 1, 2, 3, 4 or 5;

A is C or N;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, $(C_1$–$C_6)$-alkoxy-$(C_1$–$C_6)$alkyl, —S(O)$_k$—$R^{10}$ or —N($R^{11}$)($R^{12}$), wherein k, $R^{10}$, $R^{11}$ and $R^{12}$ have the same meanings as above; n and m are each independently 0 or 1; and p is 0, 1, or 2; or an agriculturally acceptable salt thereof In yet a further aspect, the compounds of this invention wherein XR is OH are useful intermediates for producing the other compounds of this invention, as well as possessing herbicidal activity.

DETAILED DESCRIPTION OF THE PREFERRED EMBODIMENTS

The novel herbicidal compounds of this invention are of the formula (I):

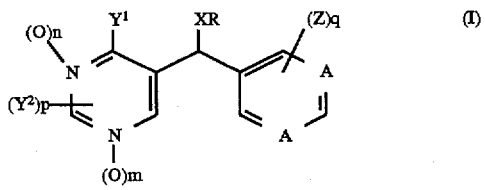

wherein: Z, q, A, X, R, Y, $R^6$, $R^7$, $R^8$, $R^9$, $R^{10}$, $R^{11}$, $R^{12}$, $R^{13}$, $R^{14}$, $R^{15}$, k, $Y^1$, $Y^2$, p, n and m have the same meaning as above; and agriculturally acceptable salts thereof.

Preferably, Z is independently halogen, $C_1$–$C_6$ alkyl, $C_1$–$C_6$ haloalkyl, $C_1$–$C_6$ alkoxy, $C_1$–$C_6$ haloalkoxy, nitro or —S(O)$_k$—($C_1$–$C_3$)alkyl wherein k is 0, 1 or 2; q is 0, 1, 2, 3, 4 or 5; and R is of the formula

wherein $R^6$ is $C_1$–$C_{12}$ alkyl, $C_1$–$C_6$ haloalkyl, phenyl or is N($R^7$)($R^8$), wherein $R^7$ and $R^8$ are each independently $C_1$–$C_{12}$ alkyl, hydrogen, $C_2$–$C_{12}$ alkenyl, $C_2$–$C_{12}$ alkynyl, $C_1$–$C_{12}$ haloalkyl, $C_1$–$C_6$ alkoxy, $(C_1$–$C_6)$alkoxy$(C_1$–$C_6)$alkyl or $R^7$ and $R^8$ together with the nitrogen to which they are bound form a morpholine, piperidine or pyrrolidine ring.

More preferably,

Z is trifluoromethyl, fluoro, chloro, bromo, iodo, methoxy, methyl or ethyl;

q is 0, 1, 2 or 3;

X is oxygen; and

R is of the formula

wherein $R^6$ is $C_1$–$C_6$ alkyl or is of the formula N($R^7$)($R^8$), wherein $R^7$ and $R^8$ are independently hydrogen, $C_1$–$C_6$ haloalkyl, $C_1$–$C_6$ alkyl, $C_2$–$C_6$ alkenyl or together $R^7$ and $R^8$ form a pyrrolidine ring.

In another aspect, this invention is directed to a herbicidal composition comprising:

(A) a compound of the formula (I):

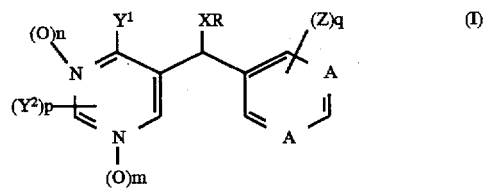

wherein: Z, q, A, X, R, Y, $R^6$, $R^7$, $R^8$, $R^9$, $R^{10}$, $R^{11}$, $R^{12}$, $R^{13}$, $R^{14}$, $R^{15}$, k, $Y^1$, $Y^2$, p, n and m have the same meaning as above; or an agriculturally acceptable salt thereof, and (B) a carrier therefor.

In yet another aspect, this invention is directed to a method for controlling undesirable vegetation comprising applying to the area where control is desired an herbicidally effective mount of a compound of the formula (I):

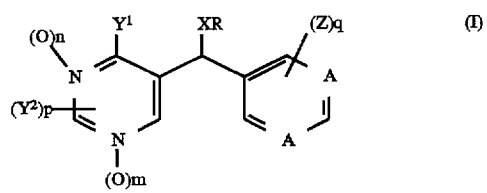

wherein: Z, q, A, X, R, Y, $R^6$, $R^7$, $R^8$, $R^9$, $R^{10}$, $R^{11}$, $R^{12}$, $R^{13}$, $R^{14}$, $R^{15}$, k, $Y^1$, $Y^2$, p, n and m have the same meaning as above; or an agriculturally acceptable salt thereof;

In yet a further aspect, because the compounds of this invention wherein XR is OH are useful intermediates for producing the other compounds of this invention, as well as possessing herbicidal activity, this invention is directed to compounds of the formula (II):

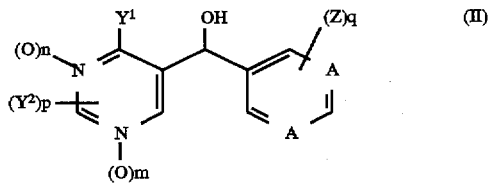

wherein: Z, q, A, X, $R^{10}$, $R^{11}$, $R^{12}$, k, $Y^1$, $Y^2$, p, n and m have the same meaning as above; or an agriculturally acceptable salt thereof.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or intermolecular hydrogen bonding, or otherwise.

The compounds of such formulae can exist in enantiomeric forms. The invention includes both individual enantiomers and mixtures of the two in all proportions.

As is employed herein, the term "hydrocarbyl", whether representing a substituent on its own or whether it is part of the definition of a larger group (e.g., as in hydrocarbyloxy, hydrocarbyl-S(O)$_k$—, etc.) is intended to include hydrocarbyl groups having from 1 to 12 carbon atoms. The term hydrocarbyl therefore includes, for example, $C_1$ to $C_{12}$ alkyl including both straight and branched chain isomers (e.g., methyl, ethyl, propyl, and hexyl); cycloalkyl of 3 to 12 carbon atoms (e.g., cyclopropyl, cyclobutyl and cyclohexyl); $C_2$ to $C_{12}$ alkenyl including for example allyl and crotyl; $C_2$ to $C_{12}$ alkynyl (e.g., propynyl); phenyl; phenylalkyl; alkylphenyl, alkenylphenyl, alkynylphenyl, alkylbenzyl, alkenylbenzyl, alkynyl benzyl, naphthyl and the like.

The term "substituted hydrocarbyl" is intended to include hydrocarbyl groups, as defined above, having one or more substituents selected from the group consisting of halogen (i.e., fluorine, chlorine, bromine, and iodine); $C_{1-4}$ alkoxy; $C_{1-4}$ alkyl-S(O)$_k$—; nitro; cyano; carboxy, and salts, amides and esters thereof; alkanoyl of 2 to 4 carbon atoms; and phenyl optionally substituted by one or more $C_{1-4}$ alkyl, $C_{1-4}$ alkoxy, $C_{1-4}$ alkyl-S(O)$_k$—, nitro, fluorine, chlorine, bromine, cyano, or $CF_3$ groups. In the above definitions, k is 0, 1 or 2.

Further, when the hydrocarbyl radical is a substituted aryl radical (e.g., phenyl, benzyl or naphthyl), the substituents may include one or more of the substituents listed in the last foregoing paragraph.

The expression "salts, amides, and esters thereof" used above in relation to carboxy substitution includes, for example, salts formed from alkali metal (e.g., sodium, potassium, and lithium), alkaline earth metals (e.g., calcium and magnesium), the ammonium ion, and substituted ammonium ions wherein one, two, three, or four of the hydrogen atoms have been replaced by optionally substituted $C_{1-6}$ hydrocarbyl moieties as defined above.

Further, in the above definitions the term "halogen" includes fluoro, chloro, bromo and iodo groups. In polyhalogenated groups the halogens may be the same or different.

The compounds of the present invention have been found to be active herbicides, possessing utility as pre-emergence and post-emergence herbicides and useful against a wide range of plant species including broadleaf, grassy and perennial species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalogen, acetic, sulfonic, phosphonic, inorganic and organic acid salts.

PREPARATION OF COMPOUNDS

The compounds of this invention are prepared by first reacting a benzoyl chloride, a nicotinoyl chloride, or in the pyrimidinyl-pyrimidine ketone case a mixed anhydride, with the magnesium enolate of an appropriate β-ketoester to form a β-triketo intermediate. This is followed by hydrolysis and decarboxylation to a β-diketone intermediate. The diketone is then converted to the alkoxy methylene or dialkylaminomethylene β-diketone by standard methods. Final ring closure to the pyrimidine is accomplished by heating with a formamidine salt and a base in an alcoholic solvent, followed by reduction to produce a 5-substituted-pyrimidine compound within the scope of formula (II).

A. Formation of the β-triketo intermediate: The β-triketo intermediate may in be generated by reacting a benzoyl chloride, a nicotinoyl chloride, or in the pyrimidinyl-pyrimidine ketone case a fixed anhydride, with a β-diketone in the presence of magnesium diethoxide (Example 1 and 8). In general, the preparation of acyl chlorides and β-diketones are described in J. March, *Advanced Organic Chemistry*, fourth edition, J. Wiley & Sons, New York (1992) pages 437–438 and 490–494 respectively. Typically, a ketoester and Mg(OEt)$_2$ are combined in a suitable solvent then heated for several hours. The solvent is then evaporated to remove the ethanol. The suitable solvent is replaced, the acid chloride or mixed anhydride added and the reaction mixture heated to complete the reaction.

B. Formation of β-diketone intermediate: The β-diketone intermediates may be generated by the decarboxylation of the β-triketo intermediates prepared in part A (Example 2). Typically, in a suitable reaction vessel such as a round bottom flask, the β-triketo intermediate is reacted with a reducing agent and a palladium catalyst to generate the β-diketone. Suitable reducing agents include hydrogen gas, tributylin hydride and NaBH$_4$. The preferred reducing agents include soluble salts of formic acid such as the combination of formic acid and triethylamine (triethylammonium formate).

If the combination of formic acid and triethylamine are used, preferably a stoichiometric amount of triethylamine and a molar excess of formic acid is used. A three fold molar excess of formic acid is especially preferred.

The preferred palladium catalyst is palladium acetate. A 20 fold molar excess of the β-triketo intermediate is used compared to the palladium acetate. Palladium zero catalysts are also quite effective allowing lower amounts of catalyst provided that the reducing agent is readily abundant and available.

A suitable solvent is added, such as tetrahydrofuran, and the reaction mixture, if necessary, is heated to reflux temperature. Although the reflux temperature is dependent upon which solvent is used, when tetrahydrofuran is used, its boiling point is about 66° C. Although tetrahydrofuran is the preferred solvent, other suitable solvents include toluene, dioxane, and dimethylformamide. The temperature is maintained and if necessary the reaction is refluxed for one to three hours. The reaction solvent is then stripped under vacuum. Subsequently, the reaction mixture is extracted with diethyl ether and then washed with water. The organic layer is dried over $MgSO_4$ and evaporated to dryness to generate the β-diketone in good yield.

C. Formation of aryl-pyrimidine ketone: The aryl-pyrimidine ketones may be prepared by first reacting the β-diketones prepared in part B above with dimethylformamide dimethylacetal to generate the dialkylaminomethylene β-diketone. Analogously, triethyl orthoformate may be used in lieu of dimethylformamide dimethylacetal to generate an ethoxymethylene β-diketone. Subsequent ring closure to the pyrimidine is accomplished by heating the methylene β-diketone intermediate with formamidine acetate in an alcoholic solvent.

In a suitable reaction vessel, a β-diketone prepared in part B above is reacted with dimethylformamide dimethylacetal in stoichiometric proportions. The solution is stirred and allowed to proceed from about 5 to about 10 hours to generate an dialkylaminomethylene β-diketone intermediate.

The dialkylaminomethylene β-diketone intermediate is added to stoichiometric amounts of a formamidine salt, such as formamidine acetate and a base, such as sodium methoxide, in a $C_1$-$C_6$ alcohol. The mixture is stirred and heated for about 1 hour. Suitable alcoholic solvents include, but are not limited to, methanol and ethanol. Subsequently, the reaction mixture is extracted with methylene chloride and then washed with water. The organic layer is dried over $MgSO_4$ and evaporated to dryness to generate the aryl-pyrimidine ketone.

D. Reduction of the aryl-pyrimidine ketone The compounds prepared in part C are reduced with a suitable reducing agent such as sodium borohydride, to produce a compound within the scope of formula (II). If sodium borohydride is used, a 2–4 molar excess of the aryl-pyrimidine ketone is used compared to the sodium borohydride.

Herbicidal derivatives of these substituted pyrimidine compounds are produced according to the general procedures which follow. The substituted-pyrimidinyl compound of formula (II), in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as a carbamoyl halide, an alkyl halide, a sulfonyl halide or a phosphoryl halide, or an alkyl or aryl acid halide, or a trialkylsilyl halide) is then added and the mixture agitated until the reaction is complete. The reaction may be quenched by the addition of an aqueous solution, and the products recovered by conventional techniques, such as extraction, filtration and the like. The product so recovered may then be purified by conventional techniques such as flash chromatography or the like.

Alternatively, the substituted-pyrimidinyl compound in suitable solvent (such as tetrahydrofuran, methylene chloride or the like) may be added to between about 2 and about 3 equivalents of an appropriate isocyanate. Between about 1 and about 100 mole percent of one or more appropriate catalysts, e.g., triethyl amine or dibutyl tin dilaurate, may be added and the reaction mixture agitated at between about 0° and 100° C. for an appropriate period (e.g., 2 to 24 hours). The product may be recovered by conventional techniques (such as extraction, filtration or the like) and may be purified by conventional techniques such as flash chromatography or the like.

The herbicidal compositions of this invention comprise a compound of formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin days, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite day, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 4-benzoylpyrazole derivatives such as pyrazoxyfen, pyrazolate and benzofenap;

D. dinitrophenols and their derivatives (e.g. acetates such as DNOC, dinoterb, dinoseb, and its ester dinoseb acetate;

E. dinitroaniline herbicides such as dinitramine, trifluralin, ethalfluralin, pendimethalin and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimetharnetryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba, and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil, and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim, sulcotrione and salts thereof, sethoxydim, cycloxydim, tralkoxydim, and clethodim;

U. sulfonyl urea herbicides such as chlorosulfuron, sulfometuron, metsulfuron and esters thereof, benzsulfuron and esters thereof such as the ester thereof methyl, DPX-M6313, chlorimuron and esters such as the ethyl ester thereof, pirimisulfuron and esters such as the methyl ester thereof, DPX-LS300, and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylpropethyl, and diflufenican;

X. amino acid herbicides such as glyphosate and glufosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

*These compounds are preferably employed in combination with a safener such as 2,2-dichloro-N,N-di-2-propenylacetamide (dichlormid).

These formulations can be applied to the areas where control is desired by conventional methods. Dust and liquid compositions, for example, can be applied by the use of powerdusters, boom and hand sprayers, and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

5% dust
  5 parts active compound
  95 parts talc

2% dust
  2 parts active compound
  1 part highly dispersed silicic acid
  97 parts talc These dusts are formed by mixing the components then grinding the mixture to the desired particle size.

5% granules
  5 parts active compound
  0.25 part epichlorohydrin
  0.25 part cetyl polyglycol ether
  3.5 parts polyethylene glycol
  91 parts kaolin (particle size 0.3–0.8 mm)

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

Wettable powders
  70%:
    70 parts active compound
    5 parts sodium dibutylnaphthylsulfonate
    3parts naphthalenesulfonic acid/phenolsulfonic acid/formaldehyde condensate (3:2:1)
    10 parts kaolin
    12 parts Champagne chalk
  40%:
    40 parts active compound
    5 parts sodium lignin sulfonate
    1 part sodium dibutylnaphthalene sulfonic acid
    54 parts silicic acid
  25%:
    25 parts active compound
    4.5 parts calcium lignin sulfate
    1.9 parts Champagne chalk/hydroxyethyl cellulose (1:1)
    1.5 parts sodium dibutylnaphthalene sulfonate
    19.5 silicic acid
    19.5 parts Champagne chalk
    28.1 parts kaolin
  25%:
    25 parts active compound
    2.5 parts isooctylphenoxy-polyethylene ethanol
    1.7 parts Champagne chalk/hydroxyethyl cellulose (1:1)
    8.3 parts sodium aluminum silicate
    16.5 parts kieselguhr
    46 parts kaolin
  10%:
    10 parts active compound
    3 parts of a mixture of sodium salts of saturated fatty alcohol sulfates
    5 parts naphthalenesulfonic acid/formaldehyde condensate
    82 parts kaolin These wettable powders are prepared by intimately mixing the active compounds with the additives in suitable mixers and grinding the resulting mixture in mills or rollers.

Emulsifiable concentrate
  25%:
    25 parts active substance
    2.5 parts epoxidized vegetable oil
    10 parts of an alkylarylsulfonate/fatty alcohol polyglycol ether mixture
    5 parts dimethylformamide
    57.5 parts xylene The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

Example 1

Preparation of aryl β-triketone (A) Preparation of the β-ketoester. To a round bottom flask equipped with an addition funnel and cold water condenser was added, 21.3 grams (0.15 mol.) of diallyl carbonate and 50 mL of tetrahydrofuran and the mixture was stirred. Next, sodium hydride, 8.4 grams (0.21 mol.), was added portion-wise. To the reaction mixture was added, 12.6 grams (0.15 mol.) of cyclopropyl methyl ketone (dissolved in 25 mL of tetrahydrofuran) via the addition funnel. The mixture was heated to reflux and heated for an additional 1 hour. Subsequently, the mixture was allowed to cool and the solvent was stripped. Next, cold water (50 mL) and 1N hydrochloric acid (50 mL) were added. The reaction mixture was transferred to a separatory funnel and diethyl ether was added. The organic layer was dried over $MgSO_4$ and stripped under vacuum to yield the β-ketoester, carboallyloxymethyl cyclopropyl ketone.

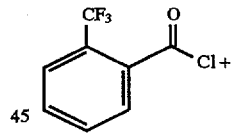

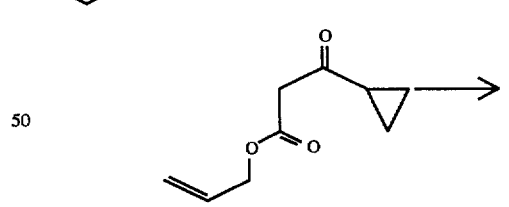

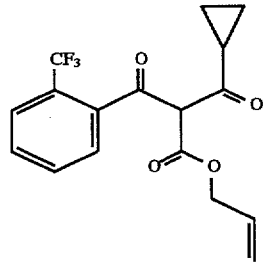

(B) Preparation of aryl β-triketone. To a round bottom flask was added 23.6 grams (0.14 mol.) of the β-ketoester, 16 grams (0.14 mol.) of magnesium ethoxide and 100 mL of tetrahydrofuran. The reaction mixture was then refluxed for 2 hours and the solvent stripped to insure complete removal of the ethanol by-product. The flask was then recharged with 100 mL of tetrahydrofuran and 29.3 grams (0.14 mol.) of the aryl acid chloride. The solution was refluxed for several hours, after which the mixture was stripped under vacuum, extracted with diethyl ether and washed with water. The 46.4 grams of β-triketone product, trifluoromethylbenzoylcarboallyloxy-methyl cyclopropyl ketone were confirmed by infrared (IR) and nuclear magnetic resonance (NMR) spectroscopy and mass spectrometry (MS).

EXAMPLE 2

Preparation of trifluoromethylbenzoylmethyl cyclopropyl ketone

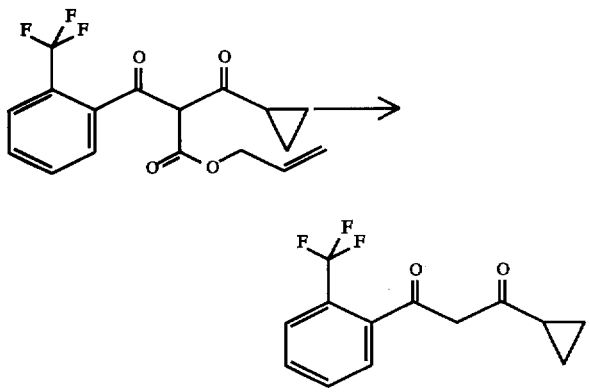

To a round bottom flask was added, 120 grams of β-triketone (0.27 mol.) (generated in Example 1), 450 mL of tetrahydrofuran, 23.3 grams of formic acid (0.62 mol.), 39.2 mL triethylamine (0.28 mol.) and 3 grams of palladium acetate (0.014 mol.). The reaction mixture was stirred and refluxed two hours. Next, an additional 10 mL of formic acid was added and the mixture refluxed for an another hour. Subsequently, 1 gram of palladium acetate and 10 additional mL of formic acid were added.

After an additional hour of reflux, the mixture was stripped under vacuum, extracted with diethyl ether and washed with water. The organic layer was dried over MgSO₄ and evaporated to dryness to yield 68.1 grams of the β-diketone, trifluoromethylbenzoylmethyl cyclopropyl ketone. The product was confirmed by infrared (IR) and nuclear magnetic resonance (NMR) spectroscopy and mass spectrometry (MS).

EXAMPLE 3

Preparation of 4-cyclopropyl-5-(1-benzyloxy-2'-trifluorobenzyl)-pyrimidine (Compound 3)

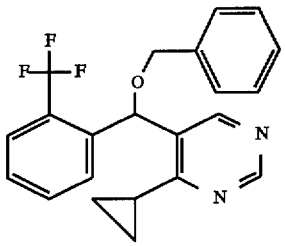

(A) 68.1 grams (0.266 mol.) of trifluoromethylbenzoylmethyl cyclopropyl ketone (example 2) were combined neat with 39.5 grams (0.297 mole) of N,N-dimethylformamide dimethyl acetal. The solution was stirred for 45 minutes and stripped to yield 82.9 grams of trifluoromethylbenzoylmethyl[(dimethylamino)methylene]cyclopropyl ketone.

(B) To a refluxing solution of 56.9 grams (0.547 mol.) formamidine acetate, 700 mL of ethanol and 125 mL (0.547 mol.) of a 25% sodium methoxide in methanol solution was added dropwise, 82.9 grams (0.267 mol.) of the product in step A. Next, the reaction mixture was refluxed 4 hours and allowed to stir over the weekend. The reaction mixture was subsequently evaporated under reduced pressure and extracted with 20 mL of dichloromethane. The evaporated product was chromatographed on a column 4 inches high and 3 inches in diameter of silica gel, with 75 mL fractions of ethyl acetate mixed with hexanes. Twenty-two fractions of 20% ethyl acetate were collected, then sixteen fractions of 50% ethyl acetate were collected. Fractions 8 through 13 were collected to yield 40.5 grams of the product, 4-cyclopropyl-5-[(2-trifluoromethyl)benzoyl]-pyrimidine.

(C) To a solution of 4-cyclopropyl-5-[(2-trifluoromethyl)-benzoyl]-pyrimidine (44.6 grams, 0.153 mol.) dissolved in 250 mL of ethanol at ambient temperature was added 2.37 grams (0.0622 mol.) of sodium borohydride. Chromatography showed the reaction to be complete 15 minutes after the addition. The mixture was evaporated under reduced pressure, extracted with dichloromethane, washed with water, dried over magnesium sulfate and evaporated under reduced pressure to yield 42.2 grams of the product, 4-cyclopropyl-5-(1-hydroxy-2'-trifluoro-methylbenzyl)-pyrimidine.

(D) 1.2 grams (0.00408 mol.) of 4-cyclopropyl-5-(1-hydroxy-2'-trifluoromethylbenzyl)-pyrimidine were combined with 0.59 mL (0.0051 mol.) of benzyl chloride in 12 mL DMF. Sodium hydride 0.11 grams (0.0047 mol.) was added portionwise. The reaction, which was complete in 1 hour, was poured over ice, extracted with dichloromethane, dried over MgSO₄, filtered and evaporated to dryness under reduced pressure to yield, 4-cyclopropyl-5-(1-benzyloxy-2'-trifluorobenzyl)-pyrimidine. The product was chromatographed on a 1 inch diameter by 4 inch silica gel column with 50% ethyl acetate/hexanes of which 20 mL fractions were collected. Fractions 4 and 8 were combined and evaporated to yield 0.75 g of Compound 3.

EXAMPLE 4

Preparation of 4-cyclopropyl-5-(1-N,N-dimethylcarbamyloxy-2'-trifluoromethylbenzyl)-pyrimidine (Compound No. 4)

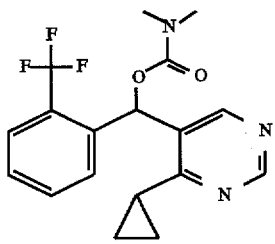

1.2 grams (0.0048 m) of 4-cyclopropyl-5-(1-hydroxy-2'-trifluoromethylbenzyl)-pyrimidine (Part C in Example 3) were combined with 0.36 grams (0.00612 mol.) of methyl isocyanate and 2 drops dibutyl tin dilaurate (catalytic) in 1 mL of dichloromethane. The mixture was stirred at ambient temperature overnight. The reaction mixture was evaporated to dryness, then chromatographed on a 1 inch diameter by 4 inch silica gel column with 50% ethyl acetate in hexanes of which 50 mL fractions were collected. Fractions 7 through 18 were combined and evaporated to yield 1.0 gram of the product, 4-cyclopropyl-5-(1-N,N-dimethylcarbamyloxy-2'-trifluoromethylbenzyl)-pyrimidine.

EXAMPLE 5

Preparation of trifluoromethylnicotinoylmethyl ethyl ketone

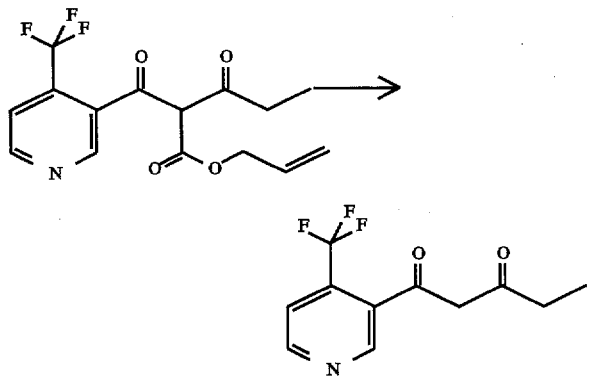

(A) Preparation of aryl β-triketone. To a round bottom flask was added 14.9 grams (0.105 mol.) of the β-ketoester (prepared by ester exchange from ethyl propionoyl acetate), 11.3 grams (0.1 mol.) of magnesium ethoxide and 150 mL of tetrahydrofuran. The solution was then refluxed for 2 hours and the solvent stripped to ensure complete removal of the ethanol by-product. The flask was then recharged with 100 mL of tetrahydrofuran and 0.095 moles of the acid chloride (prepared from 20 grams of 4-trifluoromethylnicotinic acid and oxalyl chloride). The solution was returned to reflux for several hours, after which time the reaction was stripped and worked up with dilute acid and ether. The aryl β-triketone product (22.7 grams) was confirmed by IR, NMR and MS.

(B) Preparation of trifluoromethylnicotinoylmethyl ethyl ketone. To a round bottom flask was added, 21.1 grams of the β-triketone (0.064 mol.), 110 mL tetrahydrofuran, 10 mL formic acid (0.28 mol.), 9.2 mL triethylamine (0.066 mol.) and 1 gram of palladium acetate (0.0046 mol.). The reaction mixture was stirred and refluxed one hour.

Subsequently, the mixture was stripped under vacuum, extracted with diethyl ether and washed with water. The organic layer was dried over MgSO$_4$ and evaporated to dryness to yield 14.7 grams of the β-diketone. The product was confirmed by infrared (IR) and nuclear magnetic resonance (NMR) spectroscopy and mass spectrometry (MS).

EXAMPLE 6

Preparation of trifluoromethyinicotinolymethyl cyclopropyl ketone

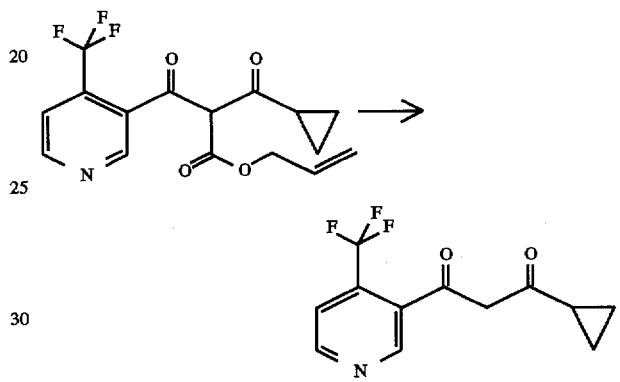

The pyridyl β-triketone in Example 5 was generated using identical reaction conditions as stated in Example 3 starting from trifluoromethylnicotinoyl chloride and the corresponding β-ketoester.

To a round bottom flask was added, 34.8 grams of the β-triketone (0.10 mol.), 175 mL tetrahydrofuran, 8.7 mL of formic acid (0.23 mol.), 14.6 mL triethylamine (0.10 mol.) and 1.1 grams palladium acetate (0.005 mol.). The reaction was stirred and refluxed for 1 hour. One equivalent of formic acid was added and the mixture refluxed an additional hour.

The mixture was stripped under vacuum, extracted with diethyl ether and washed with water. The organic layer was dried over MgSO$_4$ and evaporated to dryness to yield 25 grams of the β-diketone. The product was confirmed by infrared (IR) and nuclear magnetic resonance (NMR) spectroscopy and mass spectrometry (MS).

EXAMPLE 7

Preparation of 4-cyclopropyl-5-(1-benzyloxy-2'-trifluoromethylnicotinyl)-pyrimidine

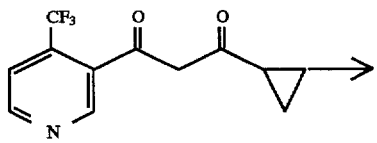

19

-continued

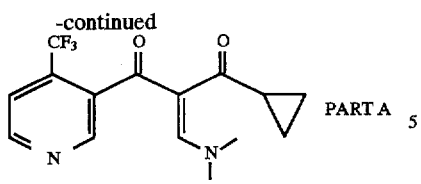
PART A (A) 25 grams (0.097mol.) of trifluoromethylnicotinoylmethyl cyclopropyl ketone (Example 6) were combined neat with 14.5 mL (0.109 mole) of N,N-dimethylformamide dimethyl acetal. The solution was stirred for 45 minutes and stripped to yield 27.9 grams of trifluoromethylnicotinoylmethyl[(dimethylamino)-methylene]cyclopropyl ketone. The product was confirmed by infrared (IR) and nuclear magnetic resonance (NMR) and mass spectrometry (MS).

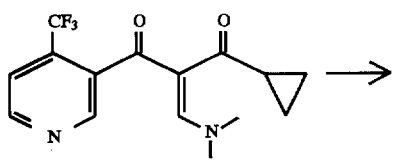

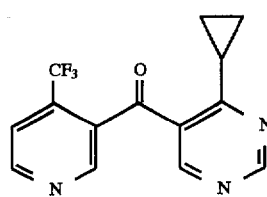
PART B (B) To a refluxing solution of 19.1 grams (0.184 mol.) formamidine acetate, 230 mL of ethanol and 42mL (0.184 mol.) of a 25% sodium methoxide in methanol solution was added dropwise, 27.9 grams (0.089 mol.) of the product in step A. Next, the reaction mixture was refluxed 4 hours and allowed to stir over the weekend. The reaction mixture was subsequently evaporated under reduced pressure and extracted with 20 mL of dichloromethane. The evaporated product was chromatographed on a column 2 inches high and 4 inches in diameter of silica gel, with 50 mL fractions of ethyl acetate mixed with hexanes. The fractions containing product were collected, to yield 8.4 grams of the product, 4-cyclopropyl-5-[(2-trifluoromethyl)nicotinoyl]-pyrimidine. The product was confirmed by infrared (IR) and nuclear magnetic resonance (NMR) and mass spectrometry (MS).

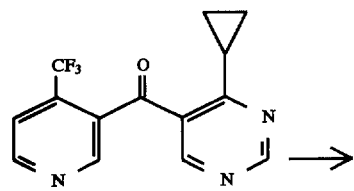

20

-continued

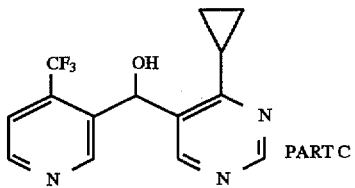
PART C (C) To a solution of 4-cyclopropyl-5-[(2-trifluoromethyl)nicotinoyl]-pyrimidine (8.4 grams, 0.0285 mol.) dissolved in 85 mL of ethanol at ambient temperature was added 0.44 grams (0.0119 mol.) of sodium borohydride. Chromatography showed the reaction to be complete 15 minutes after the addition. The mixture was evaporated under reduced pressure, extracted with dichloromethane, washed with water, dried over magnesium sulfate and evaporated under reduced pressure to yield 7.3 grams of the product, 4-cyclopropyl-5-[1-hydroxy-1-(4'-trifluoromethylpyridin-3-yl)]methyl-pyrimidine. The product was confirmed by infrared (IR) and nuclear magnetic resonance (NMR) and mass spectrometry (MS).

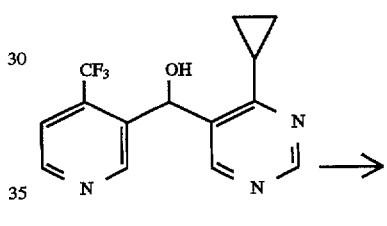

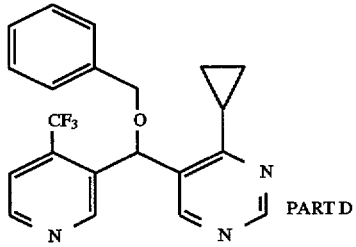
PART D (D) 1.5 grams (0.0051 mol.) of 4-cyclopropyl-5-[1-hydroxy-1-(4'-trifluoromethylpyridin-3-yl)]methyl pyrimidine were combined with 0.73 mL (0.00635 mol.) of benzyl chloride in 15 mL DMF. Sodium hydride 0.14 grams (0.00577 mol.) was added portionwise. The reaction, which was complete in 1 hour, was poured over ice, extracted with dichloromethane, dried over MgSO$_4$, filtered and evaporated to dryness under reduced pressure to yield, 4-cyclopropyl-5-(1-benzyloxy-1-(4'-trifluoromethylpyridin-3-yl)methyl pyrimidine. The product was chromatographed on a 2 inch diameter by 4 inch silica gel column with 50% ethyl acetate/hexanes of which 50 mL fractions were collected. The fractions containing product were combined and evaporated to yield 0.3 grams of the product. The product was confirmed by infrared (IR) and nuclear magnetic resonance (NMR) and mass spectrometry (MS).

EXAMPLE 8

Preparation of 4-cyclopropyl-5-(1-N,N-diethylcarbamyloxyl-1-(4-ethylpyrimidin-5-yl) methyl pyrimidine (Compound No. 64)

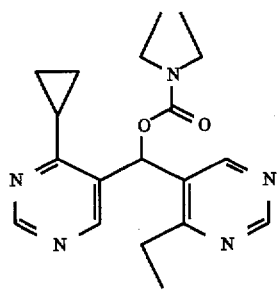

(A) To a round bottom flask was added 7.2 grams (0.0428 mol.) of the β-ketoester (see Example 1), 4.6 grams (0.4 mol.) of magnesium ethoxide and 60 mL of tetrahydrofuran. The reaction mixture was then refluxed for 3 hours and the solvent stripped to insure complete removal of the residual ethanol and generation of the β-ketoester magnesium ethoxide.

To generate the β-triketone intermediate for Compound 64, a 4-ethylpyrimidinyl mixed anhydride and the product from part A were used. The mixed anhydride was produced using the corresponding 4-ethylpyrimidinyl carboxylic acid and ethylchloroformate using the procedure outlined below in Part D.

The 4-ethylpyrimidinyl-5-carboxylic acid was generated using the procedure outlined in Parts B and C below.

(B) To a 1L round bottom flask equipped with a relux condenser, nitrogen sparge and an oil bath was added 50 grams (0.44 mol.) of ethyl propionylacetate, 65 grams (0.44 mol.) of triethyl formate and 89.8 grams (0.88 mol.) of acetic anhydride. The reaction was stirred and heated to reflux. The reaction mixture was refluxed for 2 hours and the mixture was stripped under vacuum. The resulting liquid was distilled under reduced pressure and the distillate collected (b.p. 115°–118° C.). 44 grams of the ethyl 3-oxo-2-ethoxymethylenevalerate product were collected.

(C) To a round bottom flask under a nitrogen sparge was added 4.9 grams (0.215 mol.) of sodium metal pellets gradually to 200 mL of anhydrous ethanol. The dissolved sodium metal solution was cooled to 0° C. with an ice bath. Next, 22.4 grams (0.215 mol.) of formamidine acetate was added to the mixture. Subsequently, the ester product from Part B was then added dropwise. The reaction mixture was stirred for 1 hour at 0° C. and the ice bath was removed. The round bottom flask was then equipped with a condenser and the reaction mixture was then refluxed for 1.5 hours. Afterwards the reaction mixture was again chilled to 0° C. and quenched with saturated ammonium chloride. The mixture was stripped under vacuum, and 125 mL of ethyl acetate and saturated ammonium chloride added. The organic layer was washed with water and dried with magnesium sulfate.

The resulting oil was chromatographed on silica gel using a 20–30% ethyl acetate in hexane solvent mixture. The second fraction weighing 16.9 grams was confined by infrared (IR) and nuclear magnetic resonance (NMR) spectroscopy and mass spectrometry (MS) to be ethyl 4-ethylpyrimidinyl-5-carboxylate. The ethyl pyrimidinyl carboxylate was hydrolyzed to its corresponding carboxylic acid using sodium hydroxide.

(D) 6.5 grams (0.0428 mol.) of 4-ethylpyrimidinyl-5-carboxylic acid was mixed with 70 mL of toluene and 4.3 grams (0.0428 mol.) of triethylamine. This reaction was cooled to 0° C. with the aid of an ice bath and to this mixture was added 4.6 grams (0.0428 mol.) of ethylchloroformate. The mixture was stirred at 0° C. for 1 hour and the ice bath removed. The reaction mixture continued to stir at room temperature overnight and the mixture was subsequently filtered through silica gel and cooled producing the 4-ethyl pyrimidinyl-5-carboxylic carbonic anhydride.

(E) The flask was then recharged with 20 mL of toluene and the magnesium ethoxide β-ketoester (Part A) and mixed anhydride from part D. The solution was stirred for 7 hours, after which the mixture was stripped under vacuum, extracted with diethyl ether and washed with water. The 10.3 grams of the β-triketone intermediate was confirmed by infrared (IR) and nuclear magnetic resonance (NMR) spectroscopy and mass spectrometry (MS).

(F) To a 100 mL round bottom flask was added 865 milligrams (0.0188 mol.) of formic acid, 948 milligrams (0.00939 mol.) of triethyl amine and 5 mL of tetrahydrofuran with stirring. Next, 28 milligrams (0.000125 mol.) of palladium acetate was added. 1.89 grams (0.00626 mol.) of the β-triketone intermediate from Part E was added portionwise. The reaction mixture was heated to reflux and was allowed to continue heating 3.5 hours, after which the mixture was stripped under vacuum, extracted with diethyl ether and washed with water, potassium phosphate and sodium carbonate. The β-diketone product was confirmed by infrared (IR) and nuclear magnetic resonance (NMR) spectroscopy and mass spectrometry (MS).

(G) In subsequent reactions steps, the β-diketone intermediate was reacted with dimethylformamide dimethylacetal and ring closed using formamidine acetate as in Example 7. From the bis-pyrimidine ketone, 4-cyclopropyl-5-(1-N,N-diethylcarbamyloxyl-1-(4-ethylpyrimidin-5-yl) methyl pyrimidine was generated using identical reagents and reaction conditions as in Example 4. The product was confirmed by infrared (IR) and nuclear magnetic resonance (NMR) spectroscopy and mass spectrometry (MS).

Employing processes similar to those described above, additional compounds, as listed in Table I were prepared.

TABLE I (III) structure: Y¹-pyrimidine with OR substituent, linked to Z₁/A-Z₂/A system

| CMP NO. | Y¹ | R | Z₁ | A—Z₂ | A |
|---|---|---|---|---|---|
| 1 | cyclopropyl | C(O)NHCH₃ | CF₃ | CH | CH |
| 2 | cyclopropyl | C(O)NHCH₂CH₃ | CF₃ | CH | CH |
| 3 | cyclopropyl | benzyl | CF₃ | CH | CH |
| 4 | cyclopropyl | C(O)N(CH₃)₂ | CF₃ | CH | CH |
| 5 | cyclopropyl | CH₃ | CF₃ | CH | CH |
| 6 | cyclopropyl | H | CH₂CH₃ | CH | CH |
| 7 | cyclopropyl | C(O)N(CH₃)₂ | CH₂CH₃ | CH | CH |
| 8 | cyclopropyl | C(O)C(CH₃)₃ | CH₂CH₃ | CH | CH |
| 9 | cyclopropyl | C(O)NHCH₃ | CH₂CH₃ | CH | CH |
| 10 | cyclohexyl | C(O)NHCH₂CH₃ | CF₃ | CH | CH |
| 11 | cyclohexyl | C(O)NHCH₃ | CF₃ | CH | CH |
| 12 | cyclohexyl | C(O)N(CH₃)₂ | CF₃ | CH | CH |
| 13 | cyclopropyl | H | Cl | CH | CH |
| 14 | cyclopropyl | benzyl | Cl | CH | CH |
| 15 | cyclopropyl | benzyl | CH₂CH₃ | CH | CH |
| 16 | cyclopropyl | C(O)NHCH₃ | Cl | CH | CH |
| 17 | cyclopropyl | C(O)C(CH₃)₃ | Cl | CH | CH |
| 18 | cyclopropyl | CH₂-(4-F-phenyl) | Cl | CH | CH |
| 19 | cyclopropyl | C(O)—C(CH₃)₃ | CF₃ | CH | CH |
| 20 | cyclopropyl | C(O)CH(CH₃)₂ | CF₃ | CH | CH |
| 21 | cyclopropyl | C(O)C—(CH₃)₂Cl | CF₃ | CH | CH |
| 22 | cyclopropyl | C(O)C(CH₃)₂CH₂CH₃ | CF₃ | CH | CH |
| 23 | cyclopropyl | C(O)CH(CH₃)CH₂CH₃ | CF₃ | CH | CH |
| 24 | cyclopropyl | H | CH₃ | CH | CH |
| 25 | cyclopropyl | C(O)NHCH₃ | CH₃ | CH | CH |
| 26 | cyclopropyl | benzyl | CH₃ | CH | CH |
| 27 | cyclopropyl | [full structure: 4-cyclopropyl-pyrimidine with CH₂-(2-CF₃-phenyl)] | CF₃ | CH | CH |
| 28 | cyclopropyl | [acetyl-morpholine structure] | CF₃ | CH | CH |
| 29 | cyclopropyl | C(O)NHCH₂CH₂Cl | CF₃ | CH | CH |
| 30 | cyclopropyl | C(O)—NH—SO₂-phenyl | CF₃ | CH | CH |
| 31 | cyclopropyl | C(O)NHC(O)CCl₃ | CF₃ | CH | CH |
| 32 | cyclopropyl | [pyridinyl N-oxide structure with NO₂] | CF₃ | CH | CH |
| 33 | cyclopropyl | C(O)N(CH₃)₂ | CH₃ | CH | CH |
| 34 | cyclopropyl | C(O)C(CH₃)₃ | CH₃ | CH | CH |
| 35 | cyclopropyl | [acetyl-pyrrolidine structure] | CF₃ | CH | CH |
| 36 | cyclopropyl | C(O)NHC(O)CHCl₂ | CF₃ | CH | CH |

TABLE I-continued $$\text{(III)}$$

Structure (III): pyrimidine ring with $Y^1$ at 4-position, connected via CH(OR) to C(=CH-A=Z_2)-A with $Z_1$ substituent.

| CMP NO. | $Y^1$ | R | $Z_1$ | $A-Z_2$ | A |
|---|---|---|---|---|---|
| 37 | cyclopropyl | -C(O)-N(H)-C₆H₄-O-CH (acetamido-phenoxy group) | $CF_3$ | CH | CH |
| 38 | cyclopropyl | $C(O)NHCH_3$ | $CH=CH_2$ | CH | CH |
| 39 | cyclopropyl | -C(O)-C(cyclopropyl with CH₂) | $CF_3$ | CH | CH |
| 40 | cyclopropyl | C(O)phenyl | $CF_3$ | CH | CH |
| 41 | cyclopropyl | $C(O)C(CH_2)CH_3$ | $CF_3$ | CH | CH |
| 42 | cyclopropyl | -C(O)-(furan-2-yl) | $CF_3$ | CH | CH |
| 43 | cyclopropyl | H | H | C—$CH_3$ | CH |
| 44 | cyclopropyl | benzyl | H | C—$CH_3$ | CH |
| 45 | cyclopropyl | $C(O)NHCH_3$ | H | C—$CH_3$ | CH |
| 46 | cyclopropyl | H | Br | CH | CH |
| 47 | cyclopropyl | $C(O)N(CH_3)_2$ | Br | CH | CH |
| 48 | cyclopropyl | benzyl | Br | CH | CH |
| 49 | cyclopropyl | $C(O)C(CH_2)CH_3$ | $CF_3$ | CH | CH |
| 50 | cyclopropyl | $C(O)N(CH_3)_2$ | $CH=CH_2$ | CH | CH |
| 51 | cyclopropyl | $C(O)C(CH_3)_3$ | Br | CH | CH |
| 52 | cyclopropyl | H | Cl | C—Cl | CH |
| 53 | cyclopropyl | $C(O)C(CH_3)_3$ | Cl | C—Cl | CH |
| 54 | cyclopropyl | $C(O)N(CH_3)_2$ | Cl | C—Cl | CH |
| 55 | cyclopropyl | benzyl | Cl | C—Cl | CH |
| 56 | cyclopropyl | $C(O)NHCH_3$ | Cl | C—Cl | CH |
| 57 | cyclopropyl | $C(O)NHCH_2CH_3$ | Cl | C—Cl | CH |
| 58 | cyclopropyl | $C(O)N(CH_3)OCH_3$ | Cl | C—Cl | CH |
| 59 | cyclopropyl | $C(O)NHCH_2CH_3$ | $CF_3$ | CH | N |
| 60 | cyclopropyl | $C(O)NHCH_3$ | $CF_3$ | CH | N |
| 61 | cyclopropyl | benzyl | $CF_3$ | CH | N |
| 62 | cyclopropyl | pyridine N-oxide group | $CF_3$ | CH | N |
| 63 | cyclopropyl | pyridin-2-ylmethyl | $CF_3$ | CH | N |
| 64 | cyclopropyl | $C(O)N(CH_2CH_3)_2$ | $CH_2CH_3$ | N | N |

HERBICIDAL SCREENING TESTS

The compounds listed in the foregoing table were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat. Seeding depths ranged from 1.0 to 1.5 cm and plant densities ranged from 3 to 25 plants per row depending on individual plant species.

The grass weeds planted were broadleaf signalgrass (Brachiaria platyphylla) "BRAPP"; large crabgrass (*Digitaria sanguinalis*) "DIGSA"; barnyardgrass (*Echinochloa crusgalli*) "ECHCG"; rigid ryegrass (*Lolium rigidum*) "LOLRI", fall panicum (*Panicum dichotomiflorum*) "PANDI"; giant foxtail (*Setari faberi*) "SETFA"; green foxtail (*Setaria viridis*) "SETVI" and Johnsongrass (*Sorghum halepense*) "SORHA".

The broadleaf weeds planted were velvetleaf (*Abutilon theophrasti*) "ABUTH"; redroot pigweed (*Amaranthus retroflexus*) "AMARE"; common lambsquarters (*Chenopodium album*) "CHEAL"; ivyleaf morningglory (*Ipomoea hederacea*) "IPOHE"; common purslane (*Portulaca oleracea*) "POROL" and common cocklebuff (*Xanthium strumarium*) "XANST". Additionally, yellow nutsedge (*Cyperus esculentus*) "CYPES" nutlets were also sown.

Solutions of the test compounds were prepared by weighing out an appropriate amount of the test compound to provide an application rate of 0.25 kilograms per hectare (kg/ha), then dissolving the compound in a 50:50 mixture of deionized water and acetone containing 0.5% v/v Tween 20® (polyoxyethylene sorbitan monolaurate emulsifier) as a surfactant. Additional solvents, not exceeding 15% of spray volume, were used if needed to dissolve the compound.

The soil surface was sprayed inside an enclosed linear spray table with the nozzle set above the soil line. The spray table was calibrated to deliver 400 L/ha with the application rate being 0.25 kg/ha. After treatment, the flats were placed into a greenhouse and watered as needed. The greenhouse environmental systems provided the plants with natural and artificial lighting to attain 14 hours of light per day. Day and night temperatures were maintained at 29° and 21 ° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The results of the pre-emergence screening tests are shown in Tables II (grass weeds) and II(a) (broadleaf weeds and nutsedge) below. The control ratings range from 0 to 100 percent, where 0 represents no effect with growth equal to the untreated control and where 100 represents complete kill. The symbol "—" indicates that no test was performed at the 0.25 kg/ha level of application. Compound 64 was screened at the 0.125 kg/ha rate.

TABLE II

PRE-EMERGENCE SCREENING

| CMP. NO. | BRAPP | SETVI | DIGSA | ECHCG | LOLRI | PANDI | SETFA | SORHA |
|---|---|---|---|---|---|---|---|---|
| 1 | 100 | 100 | 100 | 100 | 98 | 100 | 100 | 100 |
| 2 | 100 | 100 | — | 100 | 90 | 100 | 100 | 100 |
| 3 | 100 | 100 | — | 100 | 80 | 98 | 98 | 65 |
| 4 | 99 | 100 | — | 100 | 99 | 99 | 99 | 100 |
| 5 | 10 | 0 | — | 15 | 0 | 0 | 0 | 15 |
| 7 | 100 | 100 | 100 | 100 | 98 | 100 | 100 | 100 |
| 8 | 100 | 100 | 100 | 100 | 99 | 100 | 99 | 85 |
| 9 | 70 | 100 | 100 | 100 | 95 | 100 | 100 | 99 |
| 10 | 88 | 99 | 88 | 95 | 12 | 88 | 68 | 55 |
| 11 | 64 | 99 | 99 | 100 | 15 | 99 | 98 | 75 |
| 12 | 40 | 99 | 98 | 100 | 0 | 98 | 98 | 62 |
| 14 | 90 | 99 | 98 | 99 | 5 | 90 | 98 | 37 |
| 15 | 0 | 0 | 0 | 0 | 0 | 0 | 0 | 0 |
| 16 | 95 | 100 | 100 | 100 | 70 | 100 | 100 | 65 |
| 17 | 85 | 100 | 98 | 100 | 65 | 100 | 100 | 65 |
| 18 | 35 | 98 | 15 | 95 | 20 | 90 | 98 | 40 |
| 19 | 100 | 100 | 100 | 100 | 55 | 100 | 99 | 98 |
| 20 | 15 | 100 | 99 | 100 | 0 | 100 | 90 | 10 |
| 21 | 70 | 100 | 99 | 100 | 5 | 100 | 99 | 37 |
| 22 | 5 | 100 | 99 | 100 | 15 | 100 | 98 | 25 |
| 23 | 60 | 100 | 99 | 100 | 10 | 100 | 99 | 40 |
| 25 | 100 | 100 | 98 | 100 | 5 | 100 | 100 | 88 |
| 26 | 80 | 100 | 98 | 100 | 0 | 100 | 98 | 88 |
| 28 | 100 | 100 | 100 | 100 | 99 | 100 | 100 | 100 |
| 29 | 100 | 100 | 99 | 100 | 38 | 100 | 99 | 99 |
| 31 | 0 | 97 | 90 | 15 | 0 | 98 | 98 | 28 |
| 32 | 98 | 100 | 97 | 5 | 12 | 100 | 98 | 10 |
| 33 | 95 | 100 | 98 | 100 | 20 | 100 | 100 | 70 |
| 34 | 85 | 100 | 95 | 100 | 70 | 100 | 100 | 60 |
| 35 | 100 | 100 | 100 | 100 | 100 | 100 | 100 | 100 |
| 36 | 30 | 98 | 95 | 25 | 20 | 98 | 60 | 45 |
| 37 | 25 | 80 | 98 | 15 | 0 | 100 | 95 | 80 |
| 38 | 80 | 100 | 80 | 40 | 40 | 85 | 100 | 50 |
| 39 | 40 | 100 | 100 | 100 | 80 | 100 | 100 | 60 |
| 40 | 50 | 55 | 25 | 15 | 0 | 90 | 85 | 10 |
| 41 | 20 | 0 | 60 | 0 | 0 | 50 | 0 | 0 |
| 42 | 20 | 0 | 10 | 0 | 0 | 90 | 0 | 0 |
| 44 | 20 | 25 | 0 | 0 | 0 | 0 | 0 | 0 |
| 45 | 0 | 0 | 0 | 0 | 0 | 0 | 0 | 0 |
| 47 | 90 | 100 | 100 | 100 | 20 | 100 | 100 | 95 |
| 48 | 20 | 100 | 70 | 15 | 10 | 20 | 100 | 35 |
| 49 | 0 | 15 | 0 | 0 | 0 | 10 | 10 | 10 |
| 50 | 85 | 100 | 100 | 100 | 60 | 100 | 100 | 100 |
| 51 | 35 | 100 | 98 | 80 | 20 | 98 | 100 | 25 |

TABLE II-continued

PRE-EMERGENCE SCREENING

| CMP. NO. | BRAPP | SETVI | DIGSA | ECHCG | LOLRI | PANDI | SETFA | SORHA |
|---|---|---|---|---|---|---|---|---|
| 53 | 40 | 85 | 75 | 35 | 10 | 100 | 75 | 40 |
| 54 | 95 | 95 | — | 100 | 0 | 100 | 95 | 100 |
| 55 | 40 | 95 | 50 | 65 | 0 | 40 | 95 | 35 |
| 56 | 98 | 100 | — | 98 | 0 | 100 | 98 | 100 |
| 57 | 95 | 100 | — | 80 | 0 | 100 | 100 | 85 |
| 58 | 50 | 98 | 100 | 35 | 0 | 100 | 90 | 30 |
| 59 | 100 | 100 | 100 | 100 | 99 | 100 | 99 | 100 |
| 60 | 100 | 100 | 100 | 100 | 99 | 100 | 100 | 100 |
| 61 | 99 | 100 | 100 | 100 | 100 | 100 | 99 | 99 |
| 62 | 98 | 100 | 98 | 95 | 90 | 100 | 100 | 60 |
| 63 | 88 | 100 | 98 | 99 | 5 | 99 | 25 | 97 |
| 64 | 30 | 90 | 70 | 60 | 20 | 100 | 50 | 30 |

TABLE II(a)

PRE-EMERGENCE SCREENING

| COMP NO. | ABUTH | AMARE | IPOHE | CHEAL | POROL | XANST | CYPES |
|---|---|---|---|---|---|---|---|
| 1 | 70 | 90 | 98 | 65 | 70 | 15 | 80 |
| 2 | 40 | 90 | 98 | 65 | 80 | 45 | 75 |
| 3 | 30 | 70 | 55 | 70 | 60 | 0 | 20 |
| 4 | 85 | 40 | 100 | 45 | 85 | 65 | 75 |
| 5 | 12 | 20 | 0 | 45 | 5 | 0 | 0 |
| 7 | 45 | 65 | 95 | 70 | 65 | 20 | 55 |
| 8 | 0 | 40 | 92 | 60 | 55 | 0 | 0 |
| 9 | 65 | 85 | 98 | 75 | 70 | 0 | 15 |
| 10 | 0 | 0 | 50 | 5 | 0 | — | 0 |
| 11 | 12 | 20 | 88 | 10 | 0 | 0 | 0 |
| 12 | 10 | 10 | 60 | 5 | 3 | 0 | 0 |
| 14 | 10 | — | 0 | 55 | 80 | 0 | 0 |
| 15 | 0 | 0 | 0 | 5 | 0 | 0 | 0 |
| 16 | 5 | 50 | 75 | 85 | 65 | 0 | 40 |
| 17 | 20 | 35 | 10 | 60 | 65 | 0 | 0 |
| 18 | 0 | 25 | 0 | 50 | 65 | 0 | 0 |
| 19 | 35 | 55 | 97 | 55 | 70 | 0 | 0 |
| 20 | 10 | 65 | 95 | 25 | 65 | 0 | 3 |
| 21 | 35 | 25 | 97 | 40 | 5 | 0 | 0 |
| 22 | 12 | 78 | 99 | 45 | 40 | 0 | 15 |
| 23 | 25 | 45 | 97 | 35 | 5 | 0 | 5 |
| 25 | 20 | 65 | 90 | 50 | 30 | 0 | 20 |
| 26 | 20 | 20 | 0 | 25 | 25 | 0 | 0 |
| 28 | 35 | 90 | 95 | 50 | 25 | 0 | 25 |
| 29 | 55 | 85 | 95 | 50 | 45 | 0 | 5 |
| 30 | 0 | 0 | 0 | 0 | 0 | 0 | 0 |
| 31 | 0 | 78 | 88 | 45 | 35 | — | 0 |
| 32 | 0 | 25 | 30 | 50 | 20 | 0 | 0 |
| 33 | 40 | 80 | 60 | 50 | 90 | 0 | 0 |
| 34 | 25 | 70 | 65 | 50 | 55 | 0 | 0 |
| 35 | 85 | 95 | 100 | 80 | 60 | 0 | 25 |
| 36 | 40 | 95 | 0 | 80 | 60 | 0 | 0 |
| 37 | 25 | 90 | 10 | 80 | 70 | 0 | 0 |
| 38 | 10 | 15 | 25 | 60 | 0 | 0 | 0 |
| 39 | 40 | 60 | 40 | 80 | 45 | 0 | 10 |
| 40 | 20 | 60 | 0 | 20 | 100 | 0 | 50 |
| 41 | 0 | 30 | 20 | 10 | 0 | 0 | 0 |
| 42 | 0 | 45 | 0 | 30 | 0 | 0 | 0 |
| 44 | 0 | 0 | 0 | 0 | 0 | 0 | 0 |
| 45 | 0 | 0 | 0 | 0 | 0 | 0 | 0 |
| 47 | 55 | 35 | 98 | 80 | 25 | 0 | 5 |
| 48 | 0 | 20 | 10 | 25 | 10 | 0 | 0 |
| 49 | 0 | 0 | 0 | 0 | 0 | 0 | 0 |
| 50 | 10 | 20 | 90 | 70 | 20 | 0 | 10 |
| 51 | 0 | 20 | 5 | 50 | 25 | 0 | 0 |
| 53 | 10 | 30 | 5 | 15 | 20 | — | 0 |
| 54 | 25 | 55 | 65 | 70 | 5 | 0 | 0 |
| 55 | 30 | 40 | 0 | — | 10 | 0 | — |
| 56 | 60 | 65 | 85 | 95 | 50 | 20 | — |
| 57 | 20 | 65 | 25 | 80 | 40 | 0 | 0 |
| 58 | 0 | 50 | 0 | 55 | 20 | 0 | 0 |

TABLE II(a)-continued

PRE-EMERGENCE SCREENING

| COMP NO. | ABUTH | AMARE | IPOHE | CHEAL | POROL | XANST | CYPES |
|---|---|---|---|---|---|---|---|
| 59 | 60 | 65 | 98 | 88 | 98 | 20 | 100 |
| 60 | 65 | 75 | 98 | 85 | 90 | 30 | 85 |
| 61 | 85 | 38 | 92 | 75 | 99 | 0 | 0 |
| 62 | 0 | 90 | 10 | 80 | 85 | 0 | 15 |
| 63 | 55 | 75 | 88 | 65 | 40 | 0 | 0 |
| 64 | 20 | 15 | 40 | 5 | 10 | — | 0 |

POST-EMERGENCE HERBICIDAL EVALUATION

The soil was prepared and seeded with 10 of the same species and methodology described for the pre-emergence test. Post-emergence flats were placed in the greenhouse under the same environmental conditions as described for the pre-emergence flats and watered as needed. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 0.25 kg/ha, except compound 64 which was screened at the 0.125 kg/ha rate. Treated plants were then returned to a greenhouse and watered daily without wetting the foliage. The degree of weed control was evaluated 17–21 days after application and recorded as percentage of control as compared to the growth of the same species in an untreated control flat of the same age. The percent control scale (0–100%) used to evaluate the pre-emergence treatment was also applied to the post-emergence treatment. The post-emergence screening test results are shown in Table III below.

TABLE III

POST-EMERGENCE SCREENING

| COMP NO. | ECHCG | BRAPP | LOLRI | PANDI | SETFA | SETVI | SORHA | ABUTH | AMARE | IPOHE |
|---|---|---|---|---|---|---|---|---|---|---|
| 1 | 70 | 0 | 5 | — | 0 | 60 | 0 | 48 | 30 | 90 |
| 2 | 25 | 0 | 0 | — | 0 | 5 | 0 | 55 | 40 | 70 |
| 3 | 0 | 0 | 0 | 0 | 0 | 0 | 0 | 35 | 60 | 90 |
| 7 | 35 | 0 | 40 | 20 | 25 | 35 | 87 | 0 | 15 | 60 |
| 10 | 0 | 0 | 0 | 0 | 0 | 0 | 0 | 0 | 40 | 60 |
| 11 | 0 | 0 | 0 | 9 | 0 | 0 | 0 | 0 | 55 | 90 |
| 12 | 0 | 0 | 0 | 0 | 0 | 0 | 0 | 0 | 75 | 95 |
| 15 | 0 | 0 | 0 | 0 | 0 | 0 | 0 | 0 | 0 | 0 |
| 16 | 0 | 0 | 0 | 40 | 0 | 0 | 0 | 0 | 20 | 35 |
| 17 | 0 | 0 | 0 | 20 | 0 | 10 | 0 | 0 | 0 | 35 |
| 18 | 0 | 0 | 0 | 0 | 0 | 0 | 0 | 5 | 60 | 35 |
| 19 | 10 | 0 | 15 | 30 | 10 | 60 | 30 | 40 | 65 | 95 |
| 20 | 10 | 0 | 10 | 40 | 0 | 35 | 25 | 60 | 60 | 95 |
| 21 | 10 | 6 | 0 | 0 | 0 | 0 | 0 | 70 | 80 | 85 |
| 22 | 0 | 0 | 0 | 0 | 0 | 35 | 0 | 15 | 80 | 80 |
| 23 | 0 | 0 | 0 | 0 | 0 | 20 | 0 | 60 | 80 | 85 |
| 25 | 0 | 0 | 0 | 0 | 0 | 0 | 0 | 35 | 10 | 60 |
| 26 | 0 | 0 | 0 | 0 | 0 | 0 | 0 | 65 | 40 | 70 |
| 33 | 0 | 0 | 0 | 0 | 0 | 0 | 0 | 0 | 15 | 0 |
| 34 | 0 | 0 | 0 | 10 | 0 | 0 | 0 | 0 | 30 | 35 |
| 35 | 0 | 0 | 0 | 10 | 0 | 0 | 0 | 35 | 68 | 90 |
| 36 | 0 | 0 | 0 | 0 | 0 | 0 | 0 | 0 | 38 | 0 |
| 37 | 0 | 0 | 0 | 0 | 0 | 0 | 0 | 0 | 95 | 30 |
| 38 | 0 | 0 | 0 | 0 | 0 | 0 | 0 | 50 | 25 | 30 |
| 39 | 20 | 0 | 0 | 0 | 0 | 0 | — | 70 | 50 | 93 |
| 40 | 0 | 0 | 0 | 10 | 0 | 0 | 0 | 15 | 95 | 40 |
| 41 | 0 | 0 | 0 | 40 | 0 | 0 | 0 | 0 | 75 | 15 |
| 42 | 0 | 0 | 0 | 30 | 0 | 0 | 0 | 15 | 40 | 5 |
| 44 | 0 | 10 | 0 | 0 | 0 | 0 | 0 | 0 | 10 | 0 |
| 45 | 0 | 0 | 0 | 10 | 0 | 0 | 0 | 0 | 0 | 0 |
| 51 | 0 | 0 | 0 | 0 | 0 | 0 | 10 | 5 | 60 | 70 |
| 53 | 0 | 10 | 0 | 0 | 0 | 0 | 0 | 10 | 50 | 75 |
| 54 | 0 | 30 | 0 | 50 | 0 | 0 | 40 | 85 | 60 | 80 |
| 55 | 0 | 0 | 30 | 10 | 0 | 0 | 0 | 50 | 60 | 85 |
| 56 | 0 | 30 | 30 | 80 | 0 | 20 | 40 | 40 | 30 | 70 |
| 57 | 0 | 0 | 10 | 80 | 0 | 20 | 40 | 70 | 70 | 50 |
| 58 | 0 | 0 | 0 | 0 | 0 | 20 | 0 | 0 | 30 | 60 |
| 59 | 0 | 0 | 0 | 0 | 0 | 0 | 0 | 60 | 55 | 55 |
| 60 | 0 | 0 | 0 | 0 | 0 | 0 | 30 | 45 | 40 | 95 |

TABLE III-continued

POST-EMERGENCE SCREENING

| COMP NO. | ECHCG | BRAPP | LOLRI | PANDI | SETFA | SETVI | SORHA | ABUTH | AMARE | IPOHE |
|---|---|---|---|---|---|---|---|---|---|---|
| 61 | 0 | 55 | 10 | 65 | 0 | 15 | 0 | 98 | 70 | 95 |
| 62 | 90 | — | — | — | — | — | — | — | — | — |
| 63 | 0 | 10 | 0 | 0 | 0 | 10 | 0 | 60 | 45 | 60 |
| 64 | 25 | — | — | — | — | — | — | — | — | — |

Although the invention has been described with reference to preferred embodiments and examples thereof, it is not intended that the present invention be limited to only those described embodiments. The description of the preferred embodiments contained herein is intended in no way to limit the scope of the invention. As will be apparent to a person skilled in the art, modifications and adaptations of the above-described invention will become readily apparent without departure from the spirit and scope of the invention, the scope of which is defined and circumscribed by the appended claims.

What is claimed is:

1. A compound of the formula (I):

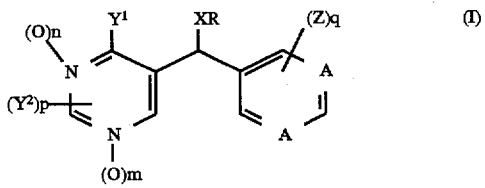

wherein

Z is independently halogen, $C_1$–$C_6$ alkyl, $C_2$–$C_6$ alkenyl, $C_2$–$C_6$ alkynyl, nitro, cyano, hydroxy, thiocyano, —$N(R^{11})(R^{12})$, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —$C(X)$—$R^{10}$ or —$S(O)_k$—$R^{10}$;

q is 0, 1, 2, 3, 4 or 5;

A is C or N;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —$C(Y)$—$R^6$, —$C(O)$—$C(O)$—$R^6$, —$S(O)_2$—$R^6$, —$P(Y)(R^{11})(R^{12})$ or —$Si(R^{13})(R^{14})(R^{15})$;

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —$N(R^7)(R^8)$;

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)-alkoxycarbonyl($C_1$–$C_6$)alkyl, hydroxycarbonyl($C_1$–$C_6$)alkyl, or $N(R^9)(R^{10})$ wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y_1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —$S(O)_k$—$R^{10}$ or —$N(R^{11})(R^{12})$, wherein k, $R^{10}$, $R^{11}$ and $R^{12}$ have the same meanings as above; n and m are each independently 0 or 1; and p is 0, 1, or 2; or an agriculturally acceptable salt thereof.

2. A compound as defined in claim 1, or an agriculturally acceptable salt thereof, wherein Z is independently halogen, $C_1$–$C_6$ alkyl, $C_1$–$C_6$ haloalkyl, $C_1$–$C_6$ alkoxy, $C_1$–$C_6$ haloalkoxy, nitro or —$S(O)_k$—($C_1$–$C_3$)alkyl wherein k is 0, 1 or 2; q is 0, 1, 2, 3, 4 or 5 and R is of the formula

wherein $R^6$ is $C_1$–$C_{12}$ alkyl, $C_1$–$C_6$ haloalkyl, phenyl or is $N(R^7)(R^8)$, wherein $R^7$ and $R^8$ are each independently $C_1$–$C_{12}$ alkyl, hydrogen, $C_2$–$C_{12}$ alkenyl, $C_2$–$C_{12}$ alkynyl, $C_1$–$C_{12}$ haloalkyl, $C_1$–$C_6$ alkoxy, ($C_1$–$C_6$)alkoxy($C_1$–$C_6$)alkyl or $R^7$ and $R^8$ together with the nitrogen to which they are bound form a morpholine, piperidine or pyrrolidine ring.

3. A compound as defined in claim 1, or an agriculturally acceptable salt thereof, wherein Z is trifluoromethyl, fluoro, chloro, bromo, iodo, methoxy, methyl or ethyl;

q is 1, 2 or 3;

R is of the formula

wherein $R^6$ is $C_1$–$C_6$ alkyl or is of the formula $N(R^7)(R^8)$, wherein $R^7$ and $R^8$ are independently hydrogen, $C_1$–$C_6$ haloalkyl, $C_1$–$C_6$ alkyl, $C_2$–$C_6$ alkenyl or together $R^7$ and $R^8$ form a pyrrolidine ring.

4. A compound as defined in claim 1, wherein X is oxygen and R is hydrogen.

5. A compound according to claim 1, of the formula:

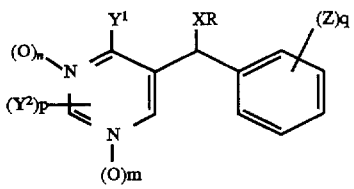

wherein

Z is independently halogen, $C_1$–$C_6$ alkyl, $C_2$–$C_6$ alkenyl, $C_2$–$C_6$ alkynyl, nitro, cyano, hydroxy, thiocyano, —$N(R^{11})(R^{12})$, $C_1$–$C_6$ haloalkyl, $C_1$–$C_6$ alkoxy, $C_1$–$C_6$ haloalkoxy, ($C_1$–$C_6$)alkoxy($C_1$–$C_6$)alkyl, halo($C_1$–$C_6$) alkoxy-($C_1$–$C_6$) alkyl, —C(X)—$R^{10}$ or —S(O)$_k$—$R^{10}$;

q is 0, 1, 2, 3, 4 or 5;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —$N(R^7)(R^8)$;

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)-alkoxycarbonyl($C_1$–$C_6$)alkyl, hydroxycarbonyl($C_1$–$C_6$)alkyl, or $N(R^9)(R^{10})$ wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —S(O)$_k$—$R^{10}$ or —$N(R^{11})(R^{12})$, wherein k, $R^{10}$, $R^{11}$ and $R^{12}$ have the same meanings as above; n and m are each independently 0 or 1; and p is 0, 1, or 2; or an agriculturally acceptable salt thereof.

6. A compound according to claim 1 of the formula:

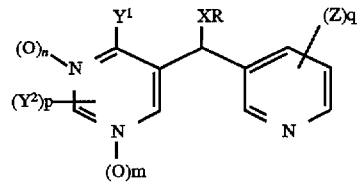

wherein

Z is independently halogen, $C_1$–$C_6$ alkyl, $C_2$–$C_6$ alkenyl, $C_2$–$C_6$ alkynyl, nitro, cyano, hydroxy, thiocyano, —$N(R^{11})(R^{12})$, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —C(X)—$R^{10}$ or —S(O)$_k$—$R^{10}$;

q is 0, 1, 2, 3 or 4;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O)—C(O)—$R^6$, —S(O)$_2$—$R^6$, —P(Y)($R^{11}$)($R^{12}$) or —Si($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —$N(R^7)(R^8)$;

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)-alkoxycarbonyl($C_1$–$C_6$)alkyl, hydroxycarbonyl($C_1$–$C_6$)alkyl, or $N(R^9)(R^{10})$ wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —S(O)$_k$—$R^{10}$ or —$N(R^{11})(R^{12})$, wherein k, $R^{10}$, $R^{11}$ and $R^{12}$ have the same meanings as above; n and m are each independently 0 or 1; and p is 0, 1, or 2; or an agriculturally acceptable salt thereof.

7. A compound according to claim 1, of the formula:

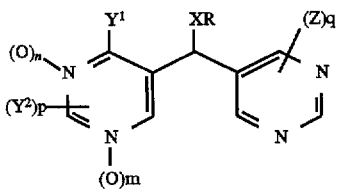

wherein

Z is independently halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$) alkoxy-($C_1$–$C_6$)alkyl, —C(X)—$R^{10}$ or —S(O)$_k$—$R^{10}$;

q is 0, 1, 2 or 3;

X is oxygen or sulfur;

R is hydrogen, hydrocarbyl, hydrocarbyl substituted with one or more of halogen or $C_1$–$C_6$ alkoxy, pyridyl, substituted pyridyl, azabenzyl, pyrimidinyl, substituted pyrimidinyl or is of the formula —C(Y)—$R^6$, —C(O) —C(O)—$R^6$, —S(O)$_2$—$R^6$, —P(Y)($R^{11}$)($R^{12}$) or —Si ($R^{13}$)($R^{14}$)($R^{15}$);

wherein

Y is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S—, furyl or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)-alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl, phenyl or substituted phenyl;

or $R^7$ and $R^8$ together with the nitrogen to which they are bound form an aziridine, piperazine, morpholine, thiomorpholine, thiomorpholine 1-oxide, thiomorpholine 1-1,dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl; and k is 0, 1 or 2;

$Y^1$ is $C_3$–$C_6$ cycloalkyl;

$Y^2$ is independently $C_1$–$C_6$ alkyl, $C_3$–$C_6$ cycloalkyl, $C_1$–$C_6$ haloalkyl, $C_1$–$C_6$ alkoxy, $C_2$–$C_6$ alkenyl, $C_2$–$C_6$ alkynyl, mercapto, $C_1$–$C_6$ alkylcarbamylthio, $C_1$–$C_6$ haloalkoxy, nitro, cyano, hydroxy, thiocyano, ($C_1$–$C_6$)-alkoxy-($C_1$–$C_6$)alkyl, —S(O)$_k$—$R^{10}$ or —N($R^{11}$)($R^{12}$), wherein k, $R^{10}$, $R^{11}$ and $R^{12}$ have the same meanings as above; n and m are each independently 0 or 1; and p is 0, 1, or 2; or an agriculturally acceptable salt thereof.

8. An herbicidal composition comprising an herbicidally effective mount of a compound according to claim 1, or an agriculturally acceptable salt thereof, and an agriculturally acceptable carrier therefor.

9. An herbicidal composition comprising an herbicidally effective amount of a compound according to claim 2, or an agriculturally acceptable salt thereof, and an agriculturally acceptable carrier therefor.

10. An herbicidal composition comprising an herbicidally effective amount of a compound according to claim 3, or an agriculturally acceptable salt thereof, and an agriculturally acceptable carrier therefor.

11. An herbicidal composition comprising an herbicidally effective amount of a compound according to claim 5, or an agriculturally acceptable salt thereof, and an agriculturally acceptable carrier therefor.

12. An herbicidal composition comprising an herbicidally effective amount of a compound according to claim 6, or an agriculturally acceptable salt thereof, and an agriculturally acceptable carrier therefor.

13. An herbicidal composition comprising an herbicidally effective amount of a compound according to claim 7, or an agriculturally acceptable salt thereof, and an agriculturally acceptable carrier therefor.

14. A method for controlling undesirable vegetation comprising applying to an area where control is desired an herbicidally effective amount of a compound according to claim 1, or an agriculturally acceptable salt thereof.

15. A method for controlling undesirable vegetation comprising applying to an area where control is desired an herbicidally effective amount of a compound according to claim 2, or an agriculturally acceptable salt thereof.

16. A method for controlling undesirable vegetation comprising applying to an area where control is desired an herbicidally effective amount of a compound according to claim 3, or an agriculturally acceptable salt thereof.

17. A method for controlling undesirable vegetation comprising applying to an area where control is desired an herbicidally effective amount of a compound according to claim 5, or an agriculturally acceptable salt thereof.

18. A method for controlling undesirable vegetation comprising applying to an area where control is desired an herbicidally effective amount of a compound according to claim 6, or an agriculturally acceptable salt thereof.

19. A method for controlling undesirable vegetation comprising applying to an area where control is desired an herbicidally effective amount of a compound according to claim 7, or an agriculturally acceptable salt thereof.

* * * * *